United States Patent [19]
Zirps

[11] Patent Number: 6,062,951
[45] Date of Patent: May 16, 2000

[54] METHOD OF MAKING A SURGICAL INSTRUMENT CUTTING JAW

[75] Inventor: Christopher T. Zirps, Milton, Mass.

[73] Assignee: Endius Incorporated, Plainville, Mass.

[21] Appl. No.: 09/159,941

[22] Filed: Sep. 24, 1998

[51] Int. Cl.⁷ ...................................................... B24B 3/40
[52] U.S. Cl. ................... 451/28; 451/369; 76/82
[58] Field of Search ............... 451/28, 367, 365, 451/369, 371; 76/82, 82.2, 104.1, 119, 101.1

[56] References Cited

U.S. PATENT DOCUMENTS

| | | | |
|---|---|---|---|
| 0,793,094 | 6/1905 | Primrose | 451/364 |
| 3,533,197 | 10/1970 | Heitmuller et al. | 76/104.1 |
| 5,097,728 | 3/1992 | Cox et al. | 76/112 |
| 5,419,220 | 5/1995 | Cox | 76/104.1 |
| 5,702,420 | 12/1997 | Sterling et al. | 606/205 |
| 5,819,738 | 10/1998 | Slater | 128/751 |

*Primary Examiner*—Robert A. Rose
*Attorney, Agent, or Firm*—Tarolli, Sundheim, Covell, Tummino & Szabo L.L.P.

[57] ABSTRACT

A method includes the steps of providing fixed and movable cutting jaws for a surgical instrument, the fixed jaw having an opening in which the movable jaw is receivable; providing a fixture; placing the fixed jaw on the fixture; supporting the movable jaw on the fixture for pivotal movement relative to the fixture at a location spaced apart from the fixed jaw; pivoting the movable jaw relative to the fixture to a stop position; and grinding the movable jaw to reduce the length of the movable jaw so that the movable jaw fits within the opening in the fixed jaw.

5 Claims, 4 Drawing Sheets

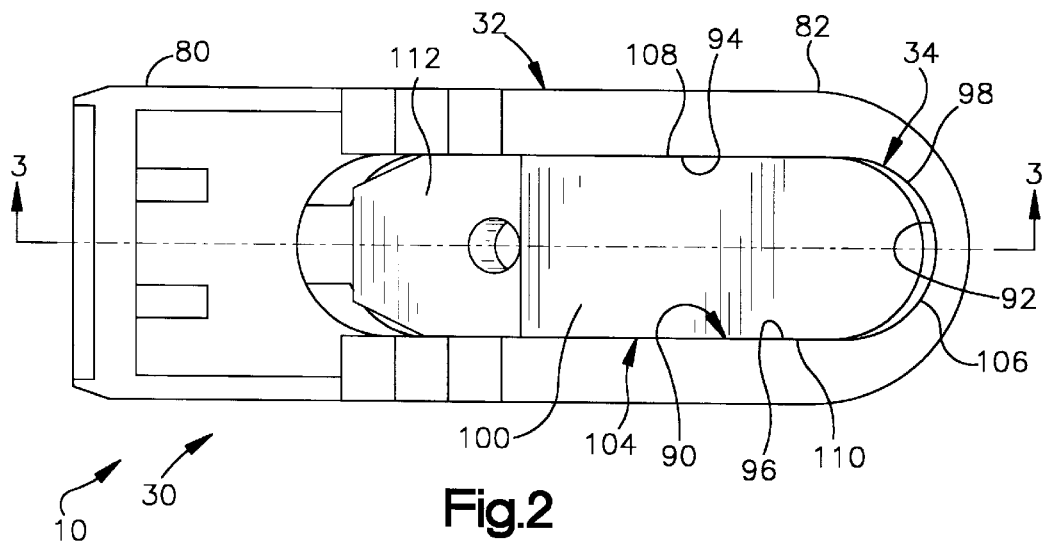
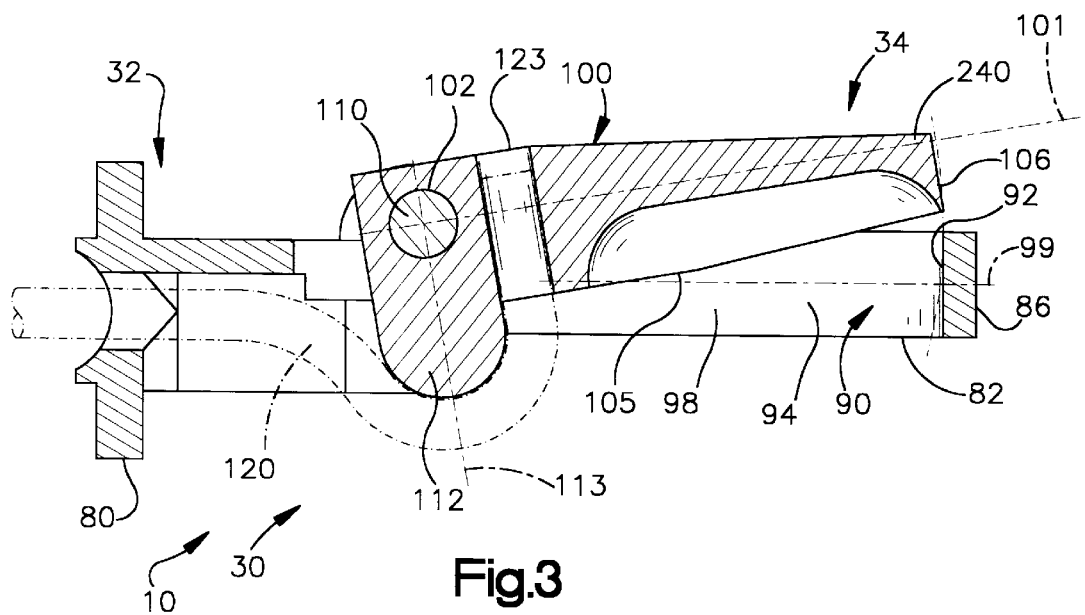

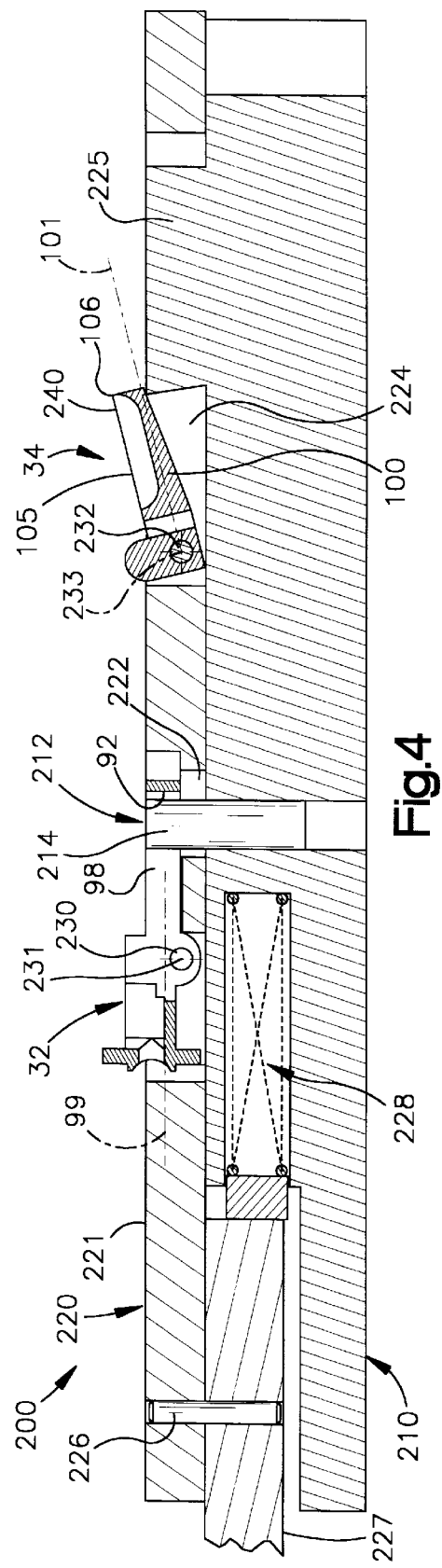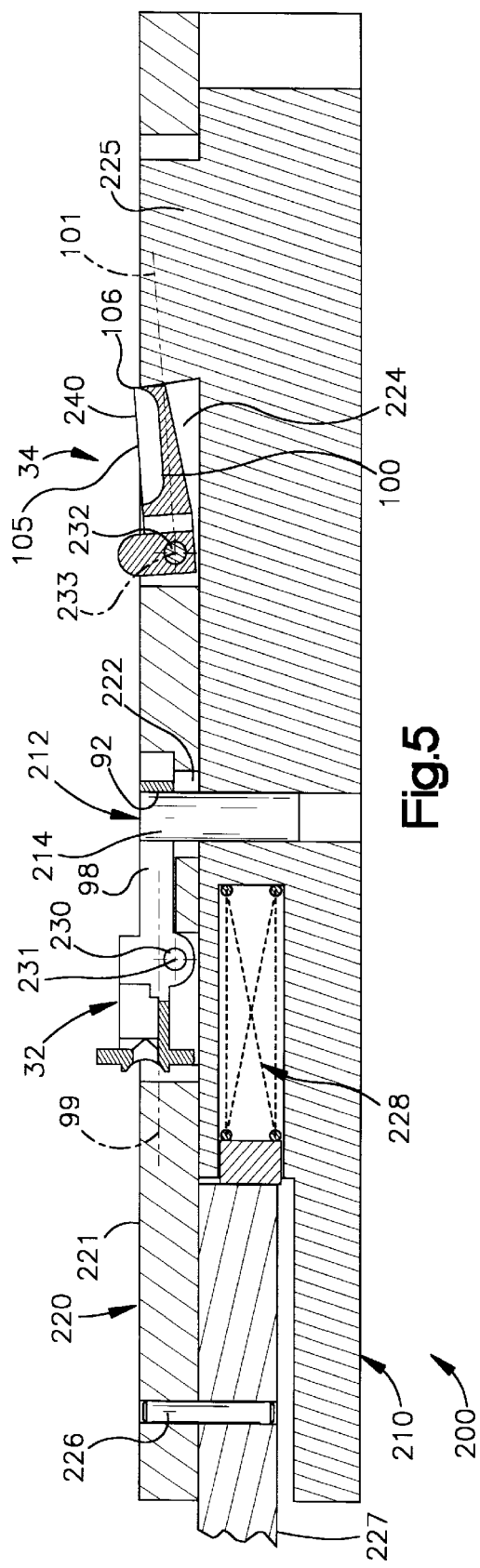

METHOD OF MAKING A SURGICAL INSTRUMENT CUTTING JAW

BACKGROUND OF THE INVENTION

The present invention relates to a surgical instrument which may be used for cutting and/or removal of tissue. In particular, the present invention relates to a surgical instrument including a pair of jaws which cooperate to cut tissue, and to a method of making a pair of jaws with extremely small clearances between them.

A disposable through cut forceps includes a pair of cutting jaws including a fixed jaw and a movable jaw. The jaws have extremely small clearances between them. Without these close clearances, the through cut jaws do not cut adequately and can jam.

Endoscopic forceps of this type are generally very small, with each jaw being no more than a few millimeters long. The cost of finishing jaws with high tolerances and close clearances can be extremely high.

SUMMARY OF THE INVENTION

The present invention is a method comprising the steps of providing fixed and movable cutting jaws for a surgical instrument, the fixed jaw having an opening in which the movable jaw is receivable; providing a fixture; placing the fixed jaw on the fixture; supporting the movable jaw on the fixture for pivotal movement relative to the fixture at a location spaced apart from the fixed jaw; pivoting the movable jaw relative to the fixture to a stop position; and grinding the movable jaw to reduce the length of the movable jaw so that the movable jaw fits within the opening in the fixed jaw.

BRIEF DESCRIPTION OF THE DRAWINGS

Further features of the present invention will become apparent to those skilled in the art to which the present invention relates from reading the following specification with reference to the accompanying drawings, in which:

FIG. 2 is an enlarged plan view of a pair of cutting jaws including a fixed jaw and a movable jaw which form part of the surgical instrument of FIG. 1;

FIG. 3 is a sectional view of the cutting jaws shown in FIG. 2;

FIG. 4 is a view partially in section of a fixture for cutting the movable jaw to a length appropriate for the fixed jaw;

FIG. 5 is a view similar to FIG. 4 showing the fixture in a second condition.

DESCRIPTION OF A PREFERRED EMBODIMENT

Figure 1:
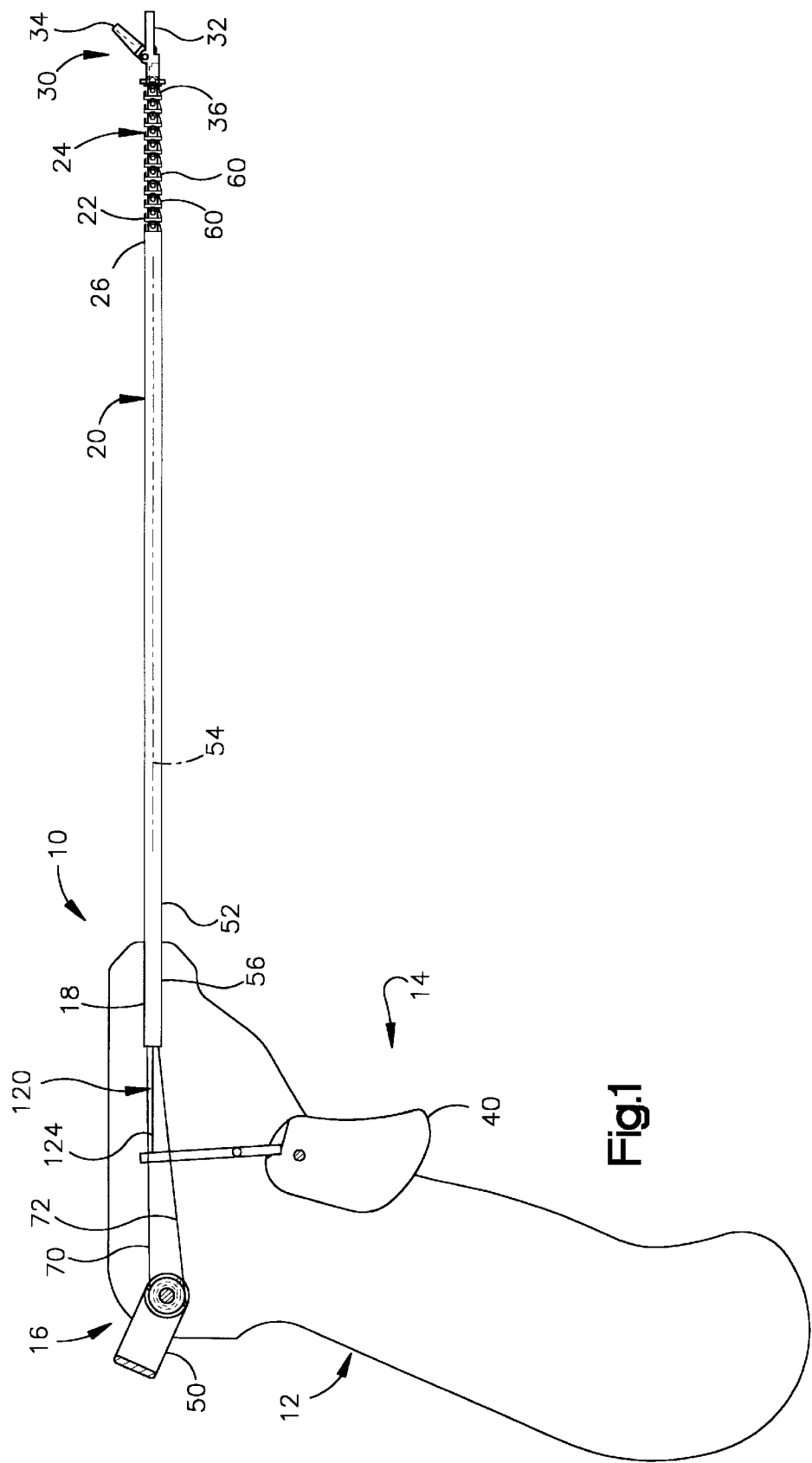
FIG. 1 is a side elevational view, with parts removed, of a surgical instrument constructed in accordance with a first embodiment of the present invention.

The present invention relates to a surgical instrument and in particular to an endoscopic surgical instrument which may be used for cutting and/or removal of tissue. The present invention is applicable to various surgical instrument constructions. As representative of the present invention, FIG. 1 illustrates a surgical instrument 10.

The surgical instrument 10 includes a handle 12 with an actuator assembly 14 and a deflection control assembly 16. A proximal end portion 18 of a first stem section or rigid stem section 20 is fixed to the handle 12. A proximal end portion 22 of a second stem section or flexible stem section 24 is connected with a distal end portion 26 of the rigid stem section 20. A surgical tool 30, including a fixed tool part 32 and a movable tool part 34, is located on a distal end portion or tip portion 36 of the flexible stem section 24.

The handle 12 of the surgical instrument 10 has a pistol grip configuration which is configured to be manually gripped by a person's hand. A trigger 40 is supported on the handle 12 for pivotal movement relative to the handle. The trigger 40 is manually engageable to effect pivotal movement of the trigger relative to the handle 12. A spring (not shown) biases the trigger 40 to an unactuated position, as shown in FIG. 1, relative to the handle 12. A deflection control lever 50 is supported on the handle 12 for pivotal movement relative to the handle, to provide the force for bending the flexible stem section 24 of the surgical instrument 10 as described below.

The rigid stem section 20 of the surgical instrument 10 includes a rigid main tube 52 which extends between and interconnects the handle 12 and the flexible stem section 24. The main tube 52 may be made from a suitable metal or plastic, as desired. The main tube 52 has a longitudinal central axis 54 which forms a longitudinal central axis of the surgical instrument 10. A proximal end portion 56 of the main tube 50 is fixed to the handle 12.

The flexible stem section 24 of the surgical instrument 10 includes a plurality of relatively pivotable vertebrae or links 60 arranged between the rigid stem section 20 and the surgical tool 30. In the illustrated embodiment, ten identical vertebrae 60 are provided. The number of vertebrae 60 can differ, depending on the desired length and amount of bending movement of the flexible stem section 24.

All the links 60 of the flexible stem section 24 are supported on the rigid stem section 20 for pivotal movement relative to the rigid stem section. The surgical tool 30 is supported on the flexible stem section 24 for pivotal movement relative to the flexible stem section and to the rigid stem section 20. The surgical tool 30, as viewed in FIG. 1, is movable in the plane of the paper. The flexible stem section 24 also preferably includes an internal member (not shown) for transmitting axial load between the surgical tool 30 and the rigid stem section 20 of the surgical instrument 10.

The surgical instrument 10 includes upper and lower deflection control wires 70 and 72 for controlling bending movement of the flexible stem section 24. The deflection control wires 70 and 72 extend through the main tube 52 and through the flexible stem section 24.

The fixed jaw 32 (FIGS. 2 and 3) of the surgical tool 30 has a support portion 80 and a cutting portion 82. The support portion 80 of the fixed jaw 32 has a pivot pin opening (not shown). The cutting portion 82 of the fixed jaw 32 includes a distal end portion 86 of the fixed jaw 32. The cutting portion 82 has an internal cutting surface 90. The cutting surface 90 has an arcuate distal end portion 92 and parallel, linear side portions 94 and 96. The cutting surface 90 defines a bullet-shaped opening 98 in the fixed jaw 32 for receiving the movable jaw 34. The cutting portion 82 of the fixed jaw 32 has a longitudinal central axis 99.

The movable jaw 34 has a generally L-shaped configuration including an elongate main body portion 100 with a longitudinal axis 101. The main body portion 100 has a pivot pin opening 102. The movable jaw 34 also has an outer peripheral side cutting surface 104. The side cutting surface 104 has an arcuate distal end portion 106 and parallel, linear side portions 108 and 110. The movable jaw 34 also has a U-shaped flat cutting surface 105 (FIGS. 3–6).

The movable jaw 34 is received in the opening 98 in the fixed jaw 32. A pivot pin 110 extends through the pivot pin opening in the fixed jaw 32 and through the pivot pin opening 102 in the movable jaw 34. The movable jaw 34 is supported on the pivot pin 110 for pivotal movement relative to the fixed jaw 32 about the pivot pin.

The L-shaped configuration of the movable jaw 34 also includes a moment arm 112 which extends from the main body portion 100 of the movable jaw, in a direction away from the pivot pin 110. The moment arm 112 has an axis 113 which extends perpendicular to the axis 101 of the main body portion 100.

The side cutting surface 104 on the movable jaw 34 is engageable with the cutting surface 90 of the fixed jaw 32 upon pivotal movement of the movable jaw relative to the fixed jaw from the open position. A small clearance is provided between the side portions 94 and 96 of the fixed jaw cutting surface 90, and the side portions 108 and 110 of the movable jaw side cutting surface 104. The arcuate portions 92 and 106 of the cutting surfaces 90 and 104, respectively, are preferably closely engageable with each other. This close engagement is achieved by cutting of the movable jaw 34 in a manner described below.

The surgical instrument 10 includes an actuator cable 120 for effecting pivotal movement of the movable jaw 34 relative to the fixed jaw 32. The actuator cable 120 is a flexible metal cable having a first end portion 122 (FIG. 3) fixed in a cable end passage 123 in the movable jaw 34 of the surgical tool 30.

The actuator cable 120 extends from the movable jaw 34 for a short distance through the fixed jaw 32 and into the flexible stem section 24. The actuator cable 120 extends for the entire length of the flexible stem section 24 and the rigid stem section 20. An end portion 124 of the actuator cable 120 is fixed for movement with the trigger 40.

When the trigger 40 is pulled, the actuator cable 120 is tensioned. The tensile force on the actuator cable 120 is transmitted into the movable jaw 34 and causes the movable jaw to pivot from the open position shown in FIG. 1 to a closed position. The movable jaw 34 moves relative to the fixed jaw 32 and relative to the flexible stem section 24.

The flexible stem section 24 of the surgical instrument 10 can be bent to a plurality of different orientations relative to the longitudinal axis 54. The surgical instrument 10 bends because of tension on one or the other of the deflection control wires 70 and 72, when the deflection control lever 50 is moved. The deflection control wires 70 and 72 (FIG. 1) are connected with the deflection control lever 50 in a manner so that pivotal movement of the control lever in a first direction relative to the handle 12 tensions the upper wire 70 and releases tension on the lower wire 72. Pivotal movement of the control lever 50 in a second direction, opposite to the first direction, releases tension on the upper wire 70 but tensions the lower wire 72. The amount of bending of the flexible stem section 24 of the surgical instrument 10 is controlled by the amount of tension on the deflection control wires 70 and 72.

The movable jaw 34 when originally manufactured is intentionally cut to be too long to fit into the opening 98 in the fixed jaw 32. The movable jaw 34 is then cut to the exact length desired in a manner described below. Each individual movable jaw 32 is cut to fit an individual fixed jaw 32, to make an accurate set of jaws for use with a surgical instrument 10.

A fixture 200 (FIGS. 4–6) is used to cut the movable jaw 34 to length. The fixture 200 includes a base 210 which is fixed in position during the cutting operation. A main pin 212 is fixed to and projects upward from the base 210. The main pin has a cylindrical outer surface 214 with a radius of curvature equal to the radius of curvature of the arcuate portion 92 of the fixed jaw cutting surface 90.

Figure 6:
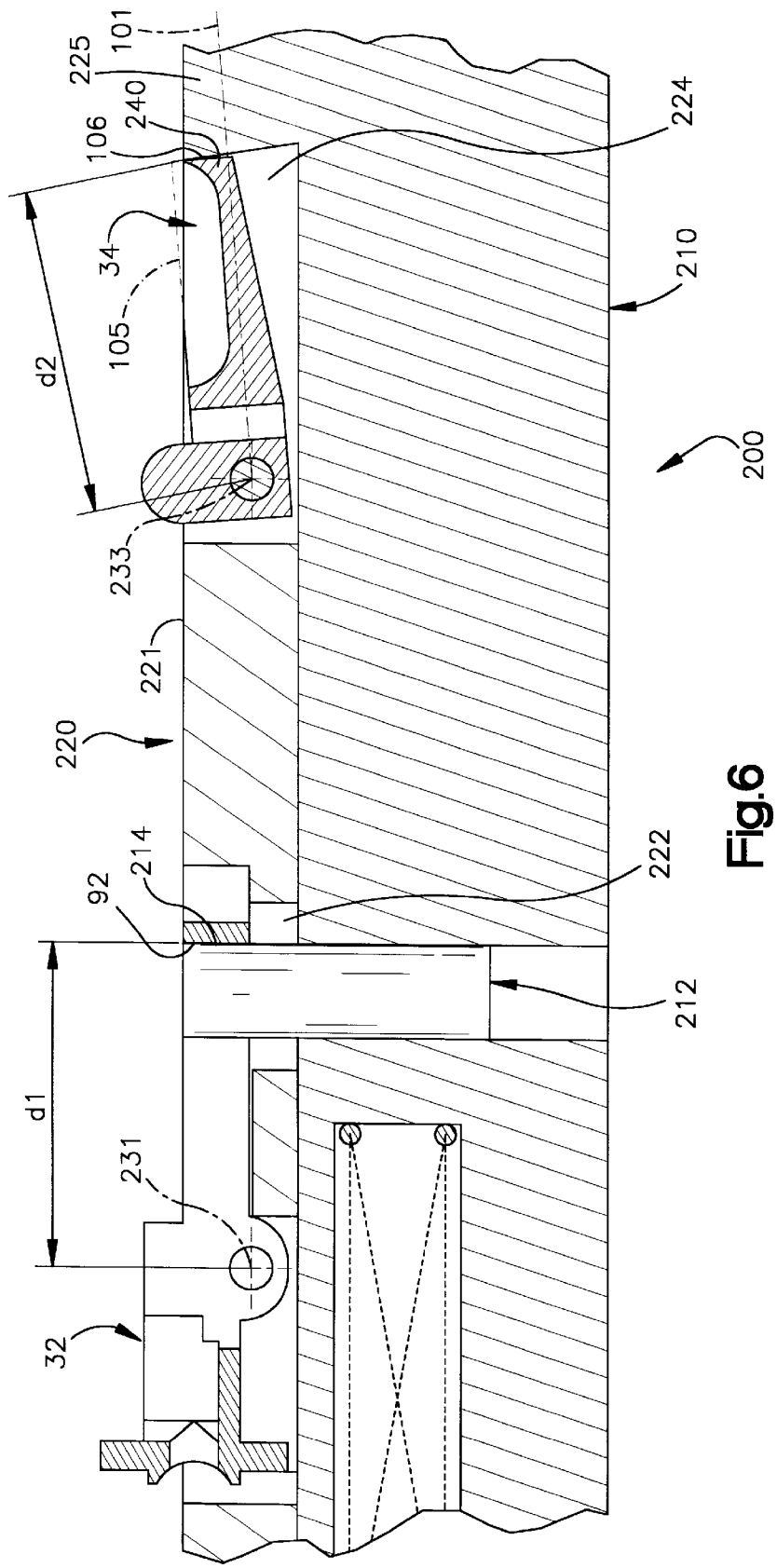
FIG. 6 is an enlarged view of a portion of FIG. 5.

A top plate 220 is supported on the base 210 for sliding movement relative to the base, in a left-right direction as viewed in FIG. 6. The top plate 220 has a planar upper side surface 221. The top plate 220 has a first opening 222 through which the main pin 212 extends. The top plate 220 also has a second opening 224, spaced apart from the first opening 222 along the length of the top plate. A portion 225 of the base 210 projects upward into the second opening 224 in the top plate 220.

The top plate 220 is connected by a pin 226 to a cam 227. The cam 227 is supported on the base 210 in a manner not shown for rotational movement relative to the base. A spring plunger assembly 228 is associated with and acts between the cam 226 and the base 210.

To make an individual set of jaws, a fixed jaw 32 is placed in the first opening 222 in the top plate 220. The longitudinal central axis 99 of the fixed jaw 32 extends parallel to the upper side surface 221 of the top plate 220.

The main pin 212 on the fixture extends through the opening 98 in the fixed jaw 32. A first temporary pivot pin 230 is placed through the pivot pin opening 84 in the fixed jaw 32 and is engaged in the top plate 220. The temporary pivot pin 230 supports the fixed jaw 32 on the top plate 220 for pivoting movement relative to the top plate about a first pivot axis 231. The first temporary pivot pin 230 also blocks longitudinal movement of the fixed jaw 32 relative to the top plate 220.

The movable jaw 34 is then placed in the second opening 224 in the top plate 220, between the top plate and the base 210. A second temporary pivot pin 232 is placed through the pivot pin opening 102 in the movable jaw 34 and is engaged in the top plate 220. The second pivot pin 232 supports the movable jaw 34 on the top plate 220 for pivoting movement relative to the top plate about a second pivot axis 233. The second pivot pin 232 also blocks longitudinal movement of the movable jaw 34 relative to the top plate 220.

The top plate 220 is next moved or slid to the left along the base 210. The fixed jaw 32 and the movable jaw 34 move with the top plate 220 relative to the base 210. The top plate 220 moves until the arcuate cutting surface 92 defining the distal end of the opening 98 in the fixed jaw 32 engages the outer side surface 214 of the main pin 212. This engagement stops the sliding movement of the fixed jaw 32, the top plate 220, and the movable jaw 34.

The cam 227 is rotated until the spring plunger assembly 228 locks the cam in position relative to the base 210. The fixed jaw 32, top plate 220, and the movable jaw 34 are thereby locked in place against linear movement relative to the base 210.

During the sliding movement of the top plate 220 relative to the base 210, the length of the second opening 224 between the fixed jaw 32 and the base portion 225 increases. The distal end 240 of the movable jaw is then manually urged downward as far as possible into the second opening 224. If the distal end 240 of the movable jaw 34 drops below the upper side surface 221 of the top plate 220, then the movable jaw is short enough for that particular fixed jaw 32, and does not need to be cut. If, on the other hand, and as is likely, the movable jaw 34 does not drop below the upper side surface 221 of the top plate 220, then it stops at a stop position relative to the top plate 222, as shown in FIG. 5. In this stop position, the axis 101 of the main body portion 100 of the movable jaw 34 does not extend parallel to the upper side surface 221 of the top plate 220.

The flat cutting surface 105 of the movable jaw 34 is then ground flush with, or parallel to, the upper side surface 221 of the top plate 220. The movable jaw 34 is thus cut along a plane which extends at an angle to the longitudinal axis 101 of the movable jaw, but parallel to the longitudinal axis 99 of the fixed jaw 32.

Because the axis 101 of the main body portion 100 of the movable jaw 34 is at an angle to (not parallel to) the upper side surface 221 of the top plate 220, the cutting of the movable jaw along this plane, in this area, reduces the length of the movable jaw. The movable jaw 34 is then the correct length for the particular fixed jaw 32 which is in the fixture 200. This occurs because the dimensions and configuration of the fixture 200 are selected so that the distance dl (FIG. 6) between the pivot axis 231 of the fixed jaw 32 and the distal cutting surface 92 on the fixed jaw, is the same as the distance d2 between the pivot axis 233 of the movable jaw 34 and the base portion 225. As a result, when the top plate 200 is positioned for a particular fixed jaw 32, a movable jaw 34 cut at that position will be the correct length to fit into the opening 98 of the fixed jaw.

By removing material from the flat cutting surface 105, the length of the movable jaw changes significantly but not its contour. The acute angle between the axis 101 and the top plate surface 221 (with which the flat cutting surface 105 is ground flush) allows the length of the movable jaw 34 to be changed by small amounts when material is removed from the flat cutting surface 105. For example, in the illustrated embodiment, 0.001" removed from the flat cutting surface 105 results in a 0.0002" reduction in the length of the movable jaw.

From the above description of the invention, those skilled in the art will perceive improvements, changes and modifications in the invention. For example, the surgical tool 30 can have a different configuration and function so long as it has a movable part and a fixed part. Such improvements, changes and modifications within the skill of the art are intended to be covered by the appended claims.

Having described the invention, we claim:

1. A method comprising the steps of:

providing fixed and movable cutting jaws for a surgical instrument, the fixed jaw having an opening in which the movable jaw is receivable;

providing a fixture;

placing the fixed jaw on the fixture;

supporting the movable jaw on the fixture for pivotal movement relative to the fixture at a location spaced apart from the fixed jaw, said location having a predetermined relationship to the position of said opening in said fixed jaw;

pivoting the movable jaw relative to the fixture to a stop position; and grinding the movable jaw to reduce the length of the movable jaw so that the movable jaw fits within the opening in the fixed jaw while the movable jaw is at said location.

2. A method as set forth in claim 1 wherein said step of grinding the movable jaw comprises the step of grinding the movable jaw along a plane extending transverse to a longitudinal axis of the movable jaw and parallel to a longitudinal axis of the fixed jaw when the fixed jaw and the movable jaw are supported on the fixture.

3. A method as set forth in claim 1 wherein the fixture includes a base assembly and said step of pivoting the movable jaw comprises the step of moving the fixed jaw with the movable jaw relative to the base until the fixed jaw engages a stop surface on the base assembly.

4. A method as set forth in claim 1 wherein the fixture includes a first member and a second member slidable relative to the first member, the first and second members defining between them an opening which varies in length during relative sliding movement of the first and second members, the movable jaw being supported at least partially in the variable length opening and pivoting into the variable length opening as it increases in length.

5. A method comprising the steps of:

providing fixed and movable cutting jaws for a surgical instrument;

the fixed jaw having an opening in which the movable jaw is receivable, the fixed jaw having an engagement surface defining one end of the opening;

the movable jaw having a first end portion for supporting the movable jaw on the fixed jaw for pivotal movement relative to the fixed jaw, a second end portion engageable with the engagement surface on the fixed jaw, and a longitudinal axis extending between the first and second end portions;

reducing the length of the movable jaw by grinding the movable jaw along a plane extending transverse to the longitudinal axis of the movable jaw.

\* \* \* \* \*